(12) United States Patent
Trembly et al.

(10) Patent No.: US 6,485,486 B1
(45) Date of Patent: Nov. 26, 2002

(54) SYSTEM AND METHODS FOR FALLOPIAN TUBE OCCLUSION

(75) Inventors: B. Stuart Trembly, Hanover, NH (US); Paul Manganiello, Norwich, VT (US); P. Jack Hoopes, Hanover, NH (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 09/463,679

(22) PCT Filed: Aug. 4, 1998

(86) PCT No.: PCT/US98/16227

§ 371 (c)(1),
(2), (4) Date: May 1, 2000

(87) PCT Pub. No.: WO99/07297

PCT Pub. Date: Feb. 18, 1999

(51) Int. Cl.[7] ............................................. A61B 18/04
(52) U.S. Cl. ........................... 606/33; 606/41; 607/101; 607/102
(58) Field of Search .................. 606/31–34, 37–42, 606/45–50; 607/100–102

(56) References Cited

U.S. PATENT DOCUMENTS

| 4,016,761 | A | * | 4/1977 | Rozzell et al. ......... 250/227.11 |
| 5,147,353 | A | | 9/1992 | Everett |
| 5,301,687 | A | * | 4/1994 | Wong et al. ................... 606/33 |
| 5,556,396 | A | | 9/1996 | Cohen et al. |
| 6,068,626 | A | * | 5/2000 | Harrington et al. ........... 606/28 |

\* cited by examiner

*Primary Examiner*—Rosiland S. Kearney
(74) *Attorney, Agent, or Firm*—Curtis A. Vock; Lathrop & Gage L.C.

(57) ABSTRACT

The invention provides systems, methods for 14 treatment, and occlusion of the fallopian tube. An elongated catheter (22) is placed into the isthmic region (14) of the fallopian tube (16) in a trans-cervical trans-uterine fashion, and a mono-pole antenna (92) is disposed within a distal end of the catheter. The antenna radiates microwave energy in resonance to a drive frequency into tissue of the isthmic region without physical contact between the mono-pole antenna, and the tissue. This heating causes occlusion after a period of time. Typically, the catheter, and the mono-pole antenna are disposable after one treatment. In the preferred embodiment, the antenna is formed from an extension of the inner conductor of a coaxial cable coupled to a microwave generator. A power control section (24) can be used to control, and apply the appropriate microwave power to the fallopian tube tissue. In addition, the invention preferably incorporates a microwave immune thermometry probe within the catheter to measure temperature of the tissue in real time.

40 Claims, 4 Drawing Sheets

SYSTEM AND METHODS FOR FALLOPIAN TUBE OCCLUSION

FIELD OF THE INVENTION

The invention relates generally to systems and methods which facilitate fallopian tube occlusion.

BACKGROUND OF THE INVENTION

In the United States, approximately 600,000 to 700,000 women undergo the form of sterilization known as laparoscopic tubal ligation each year. This frequent procedure typically involves general or regional anesthesia in an outpatient setting. A small incision is made through the 'belly-button' and also above the pubic bone. Thereafter, electrical forceps, a pair of clips or rings, are then applied to the isthmic portion of the fallopian tubes which usually results in closure.

The history of hysteroscopic fallopian tube occlusion is long and extends back to at least 1849, when Froriep tested a silver nitrate solution. Since then, many investigators have researched human fallopian tube occlusion utilizing transvaginal, transcervical, and transuterine (TVCU) approaches which can be divided into either (i) destructive-obstructive methods, or (ii) mechanical-obstructive methods. Both of these methods, however, were performed in a "blinded fashion", meaning that the operator was unable to visualize or identify the internal length of the tube, even though the beginning of the fallopian tube, i.e., the tubal "funnel", was visualized or palpated.

In the destructive-obstructive methods, for example, various caustic substances, including quinacrine and more recently methyl 2-cyanoacrylate (MCA), have been tested and utilized with varying degrees of success to damage, and hence close, the fallopian tube. MCA, for example, is delivered without anesthesia in an outpatient setting. A balloon device pushes the MCA from the uterine cavity and, if all goes well, through both fallopian tubes. Little substantive clinical data is however available to evaluate safety issues and the complication rates associated with such methods.

Other such destructive methods which attempt to damage and close the intramural portion of the fallopian tube include heat, electosurgery, and laser illumination. These methods have not gained acceptance due to (i) high failure and complication rates, (ii) the necessity of general or regional anesthesia, and (iii) the high cost and need for a skilled hysteroscopist. See, e.g., Zatuchini, *Contraceptive technologies for the future*, Current Problems in Obstet & Gynecol, 7(11) (1984).

Similarly, the mechanical-obstructive methodology for obstructing the human fallopian tube have been tested, for example, with either silastic or metal plugs. The effectiveness of these mechanical methods, however, is typically no better than those occlusion methods which attempt to destroy the fallopian tube.

In 1985, Platia and Krudy reported the first successful TVCU catherization, under hyserosalpingographic (HSG) guidance, of a suspected obstructed fallopian tube in an infertile woman, and which resulted in a subsequent pregnancy. They utilized a 3 Fr., end hole polyethylene catheter with a 0.018" pediatric guide wire. M. Platia and A. Krudy, *Transvaginal floroscopic recanalization of a proximally occluded oviduct*, Fertil & Steril, 44(4):704 (1985). This technique is now routinely utilized to treat certain types of tubal obstructions.

In 1988, a bi-polar radiofrequency catheter was developed which produced an obstructing lesion in the isthmic portion of the human falopian tube. This first generation catheter had two 1 mm electrodes separated by 1 mm. Utilizing the cat-uterine horn, a lesion of less than 1 cm was produced with inconsistent closures. A subsequent, second generation catheter bad two 3 mm electrodes separated by 3 mm. This resulted in a lesion of approximately 1 mm to 1.5 mm per electrode. Although there appeared to be closure, there was microscopic, histologic recannalization of the fallopian tube obstructing lesions. These recannalization effects raise questions concerning the occlusion efficacy and consistency using this technique.

Improvements in fallopian tube occlusion are thus sought. to improve cost effectiveness, patient safety, and reliability. For example, the widely used laparoscopic tubal ligation still has a sterilization failure rate of approximately 0.2 to 0.6%. DeStefano et al., Demographic trends in tubal sterilization: United States, 1970–1978 AJPH, 72(5), 480–484 (1982); Greenspan Jr. et al, *Tubal sterilizations performed in freestanding ambulatory-care surgical facilities in the United States in* 1980, J of Reproductive Medicine, 29(4), 237–241 (1984).

It is, accordingly, an object of this invention to provide improved methods for fallopian tube occlusion. Other objects of the invention will be apparent from the description which follows.

SUMMARY OF THE INVENTION

In one aspect, the invention provides a method for non-invasive transcervical tubal occlusion (sterilization) in women. A sterilization catheter—designed to be introduced in a transcervical-transuterine fashion—is passed into the fallopian tube either under direct visualization with a fiber optic system such as the Linear Everting Catheter (Imagyne), or fluoroscopically using standard radiologic-angiographic techniques. A microwave energy source (e.g., operating at 915 MHz) connects with an antenna contained within a disposable catheter. The catheter preferably has a diameter of approximately 2–3 mm, or smaller. The microwave antennas can be reused, but are preferably inexpensive so as to be disposable after one treatment. The treatment time (i.e., the time the energy is delivered) is approximately ten minutes. The latent period to fallopian tube occlusion is approximately 45–60 days.

In another aspect, the invention provides a system which produces sterilization through closure of the fallopian tube. The system elevates the temperature of living tissue through absorption of microwave energy. The system transfers microwave energy from a generator outside the body to the site of heating without significant deposition of energy in tissue. Preferably, the system incorporates a coaxial cable to facilitate the energy transfer. In one aspect, the applicator utilizes a monopole conductor extending from the coaxial cable and embedded in a cylinder of insulating, biocompatible material, such as polytetraflouroethylene (Teflon). Accordingly, at the heating site, the applicator couples microwave energy to the surrounding tissue without direct contact between a metal conductor and the tissue At the site of intended heating, the oscillating current and charge in the monopole conductor produces oscillating electric and magnetic fields in the surrounding tissue. The oscillating electric field causes polar molecules in tissue, such as water, to rotate in place, generating frictional heating. The presence of an overlying layer of insulating material does not prevent the formation of electric and magnetic fields in tissue, because the length of the monopole is chosen to form a resonant (or near-resonant) structure. Such a structure coordinates the electric and magnetic fields so that they sustain themselves outside the applicator. The length of such a structure is inversely proportional to the microwave frequency and is inversely proportional to the square root of a weighted average of the permittivity of the insulating layer and the surrounding tissue. For example, at 915 MHz or 2450 MHz (MHz=$10^6$ cycles/second), the length of the insulated monopole at resonance (or near-resonance) in tissue is one centimeter to several centimeters. The given values of microwave frequency are preferably those permitted by the FCC for use in industrial, scientific, or medical applications (e.g., ISM frequencies).

At frequencies less than microwave frequencies, e.g., less than 100 MHz, the length of a resonant structure is impractically long for use in the human body. Consequently, a low-frequency device, such as a radio-frequency device, must instead incorporate a metallic conductor in direct contact with tissue to permit the flow of a conduction current, which heats tissue through the translational motion of dissolved ions in tissue, not though the rotation of polar molecules. The intense conduction currents produced at the surface of a metal conductor in contact with tissue cause charring of tissue and hence poor control of the heating process. The invention thus avoids these problems.

In one aspect, the invention provides methodology which elevates the temperature of the fallopian tube in an outpatient procedure in order to produce biological responses that will cause the tube to close, preventing future pregnancy. An insulated, microwave applicator is inserted through a transvaginal-transcervical-transuterine technique so as to place the applicator tip in the fallopian tube. Microwave energy is applied to the external end of the applicator to heat fallopian tube tissue surrounding the tip. In testing of animals, it has been shown that 35 watts of microwave power at 915 MHz elevates the temperatures at the hottest point to approximately 65° C. for approximately 5 minutes. After four to six weeks, examinations show that the architecture of the uterine tissue is completely effaced at the point of maximum temperature and the lumen is closed on both sides of this region.

In one aspect, the invention provides a method for non-invasive occlusion of a fallopian tube, including the steps of: inserting an assembly of electrical conductors into the fallopian tube, the conductors forming a microwave antenna; and driving the conductors with microwave frequencies wherein the antenna emits microwave radiation that heats the fallopian tube for delayed occlusion of the fallopian tube. In a preferred embodiment, the conductors is replaced by a single monopole such as formed by a center conductor of a coaxial cable.

The method can include the further step of shielding the conductors within a distal end of a biocompatible catheter to prevent direct contact between the conductors and tissue.

Preferably, the method includes visualizing placement of the distal end within the fallopian tube through an imaging catheter during the step of inserting. Alternatively, the method can include fluoroscopically estimating placement of the distal end within the fallopian tube during the step of inserting.

Acceptable frequencies of the invention include ISM frequencies such as 915 MHz and 2450 MHz.

The step of driving typically extends for approximately five minutes; and the delayed occlusion generally occurs between approximately 30 and 60 days.

Preferably, the step of inserting the conductors includes inserting a distal end of a coaxial cable. The center conductor of the coaxial cable forms a monopole conductor which extends from the distal end of the coaxial cable for a length corresponding to a desired resonant frequency.

Typically, the method includes the step of depositing one to ten watts of microwave power in the fallopian tube (and preferably within the isthmic portion of the tube).

The method can also include the step of heating tissue within the fallopian tube to between approximately 60 and 80 degrees C. for approximately two to ten minutes.

For purposes of control, the method can include the step of measuring tissue temperature during the step of driving the conductors. A microwave-immune thermometry catheter can be used for this purpose.

The invention also provides a system for occluding the fallopian tube. An elongated catheter has a distal end for placement into the fallopian tube, and a proximal end for manipulating the catheter. An assembly of conductors, disposed within the distal end of the catheter, deposits microwave energy into tissue of the fallopian tube without physical contact between the conductors and the tissue. The microwave energy heats the tissue for subsequent tubal occlusion.

Preferably, the catheter has a diameter between about 1–3 mm. The catheter can be disposable or non-disposable after one use; and is preferably formed of a biocompatible material such as Teflon.

In one aspect, the system includes a choke attached proximal to the conductors to reduce currents flowing from the distal end back towards the proximal end of the catheter. Such a choke can include a cylindrical conductor surrounding an outer shield of the coaxial cable and separated from the shield via an insulating layer. The cylindrical conductor has a distal end positioned towards the distal end of the catheter and a proximal end positioned towards the proximal end of the catheter. A connector electrically connects the cylindrical conductor to the shield at the distal end of the choke.

Alternatively, the choke includes a cylindrical conductor surrounding an outer shield of the coaxial cable and separated from the shield via an insulating layer; the cylindrical conductor has a distal end positioned towards the distal end of the catheter and a proximal end positioned towards the proximal end of the catheter, and a connector electrically connects the cylindrical conductor to the shield at the proximal end of the choke.

In another alternative arrangement, the conductors can include one end of a center conductor of a coaxial cable, and a ground plane attached to the outer conductor of the cable and deployed in the uterous connected with the fallopian tube to reduce currents flowing from the distal end back toward the proximal end of the catheter. The ground plane can for example be formed of wires separated by less than a wavelength of the energy so as to approximate a solid ground plane effect.

These and other aspects and advantages of the invention are evident in the description which follows and in the accompanying drawings.

DETAILED DESCRIPTION OF THE INVENTION

The human fallopian tube is made up of four segments. The intramural segment, with a length of approximately 10 mm, is variably straight, curved, and sometimes tortuous. The second segment, the isthmic, is approximately 2–3 cm in length and is the area in which laparoscopic tubal ligation is usually directed. This section contains the narrowest lumen of the tube, with average thickness of about 0.4 mm, but with a potential range of 0.1–2.0 mm. It also has the thickest musculature, i.e., an inner longitudinal layer and an outer circular layer, of the extra-uterine tube. The full thickness of the wall of the isthmic portion has not been adequately determined; however, unpublished studies of hysterectomy specimens in parous females indicate a full thickness of approximately 3–4 mm. The final two fallopian tube segments consist of the ampullary and the fimbrial segments.

Figure 1:
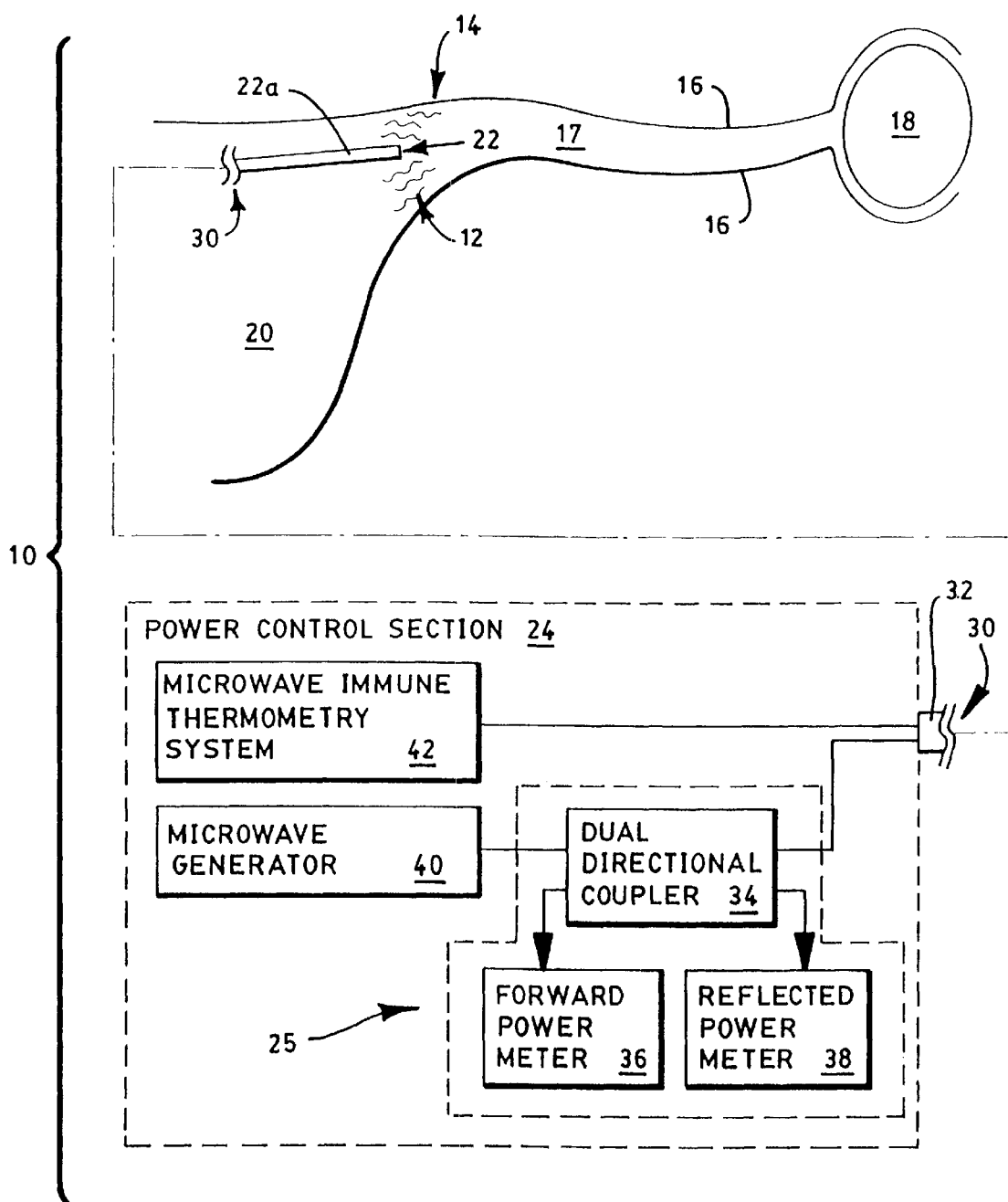
FIG. 1 shows a schematic illustration of one system for fallopian tube occlusion in accordance with the invention.
Figure 1A:
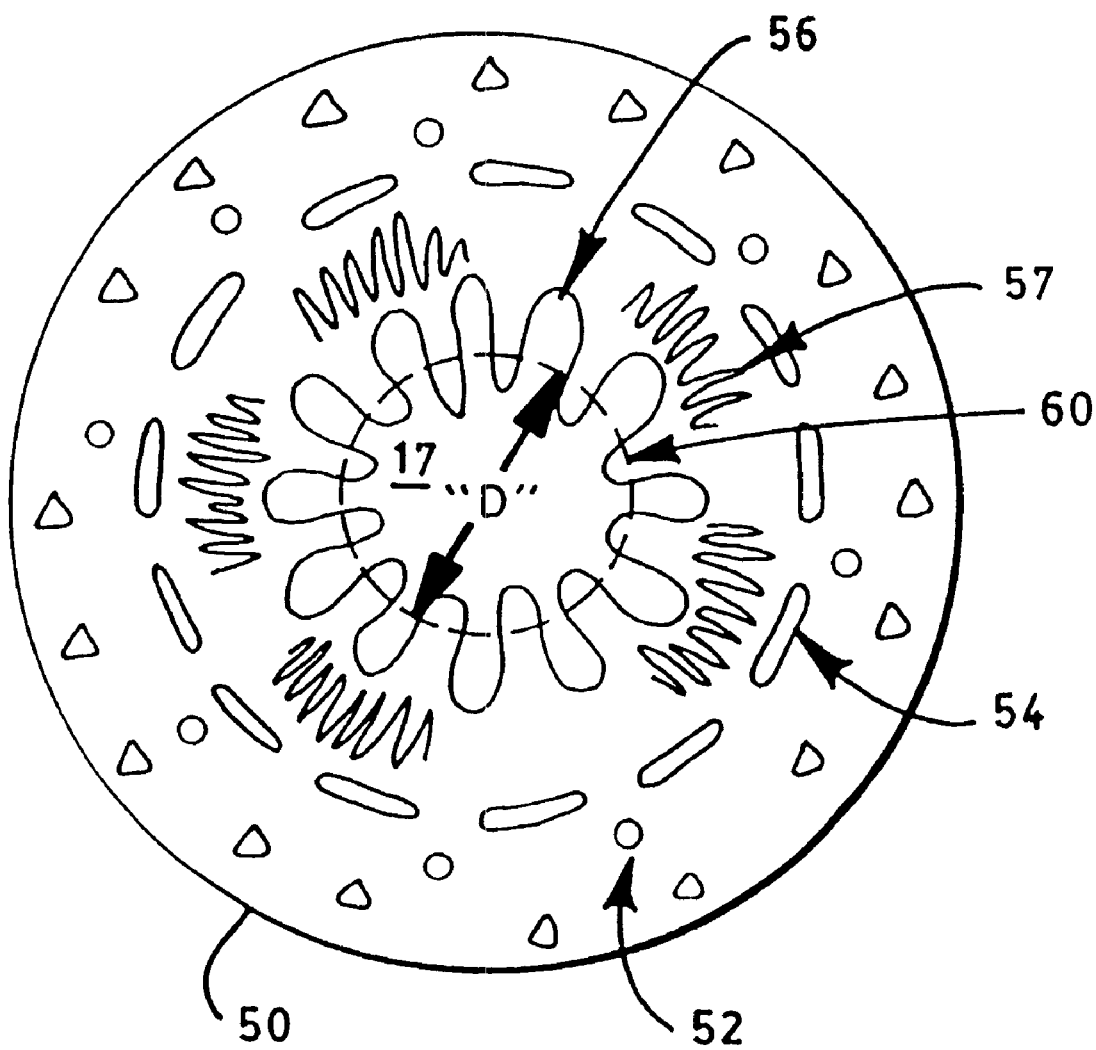
FIG. 1A schematically shows a cross-sectional view of the fallopian tube and system of FIG. 1.

FIG. 1 shows a schematic illustration of one system 10 of the invention in which microwave energy 12 is delivered locally to the isthmic section 14 of the fallopian tube 16 for tubal occlusion. The isthmic section 14 is chosen because the wall of the fallopian tube in this region is relatively thick and robust. FIG. 1A shows a cross-sectional view of the fallopian tube wall and system 10 (and particularly of the applicator 22 of system 10) at the isthmic section 14. FIG. 1 also shows the orientation and general location of the ovary 18 and uterus 20.

More particularly, FIG. 1 shows that the system 10 includes an applicator 22 and a power control section 24. For ease of illustration, the section 24 and applicator 22 are shown unconnected, while in fact the applicator body 22a flexibly extends between the fallopian tube 16 and the coupler 34. The symbol 30 thus illustrates that the applicator 22 connects integrally with the section 24. A connector 32 mates the applicator 22 with section 24.

Since the applicator 22 passes into the female body in a transcervical-transuterine fashion the diameter "D" of the applicator 22 is sufficiently small to pass through the cervix. Typically, therefore, the applicator 22 is flexible and cylindrical, with a D diameter of between 1–3 mm, or smaller.

In one embodiment, the power control section 24 contains a controller 25 (including a dual directional coupler 34, a forward power meter 36, and a reflected power meter 38) and a microwave generator 40. The generator 40 provides microwave power to the applicator 22; and the forward and reflected power meters 36, 38 provide measurement of microwave power to and from the female patient through the dual directional coupler 34. The controller 25 provides overall control of the power delivered to the patient and can include user interfaces and computerized hardware (not shown) to facilitate control.

The microwave generator 40 can for example be an AMT Model 1120 which produces 50 watts of microwave power in the channel used to power the applicator 22. The power is controlled manually by adjusting a DC voltage applied to the back panel of the generator 40. The dual directional coupler 34 diverts one-hundredth of the power applied to the applicator 22 to permit measurement of the forward power by the power meter 36. It also diverts one-hundredth of any power reflected from the applicator 22 for the same purpose by the reflected power meter 38. This serves to confirm normal operation of the applicator 22 during a procedure, since reflected power is negligible when the applicator 22 is functioning normally.

The system 10 can also include a microwave-immune thermometry system 42, though not required. The system 42 is known in the art and is for example manufactured by Luxtron in Mountain View, Calif. It contains a fiber optic probe that is approximately 0.5 mm in diameter and that feeds into a second lumen of the applicator 22 (described in more detail below). The probe permits measurement of the temperature of tissue adjacent to the applicator 22 during treatment to confirm conformance to treatment protocols such as described herein.

As used herein, "applicator" operates similar to a catheter. Further detail of catheters may be ascertained with reference to PCT application WO 92/11895, which is incorporated herein by reference.

FIG. 1A illustrates further detailed features of the fallopian tube 16 of FIG. 1 in a cross-sectional view. The outside of the tube 16 includes a serosal lining 50 which encloses the longitudinal muscle fibers 52, circular muscle fibers 54, mucosal folds 56, lamina propria 57 and lumen 17. Also illustrated is a schematic outline 60 of the applicator 22 in operational position within the tube lumen 17.

Figure 2:
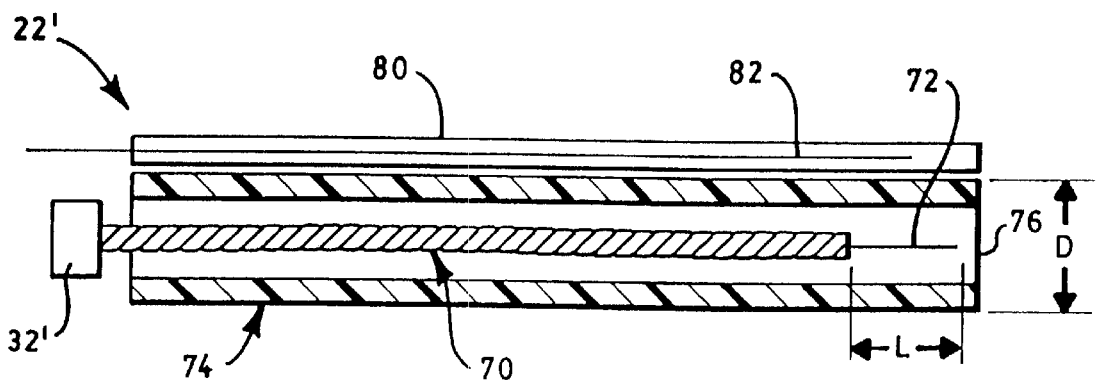
FIG. 2 shows a cross-sectional side view of one applicator of the invention.

FIG. 2 illustrates one applicator 22' constructed according to the invention. The connector 32' provides for connection to the dual directional coupler 34. The applicator 22' is constructed by removing the outer shield from one end of a piece of flexible coaxial cable 70. This exposes the insulating layer, inside of which is the inner conductor 72. The inner conductor 72 forms the monopole which couples microwave energy 12 into surrounding tissue. The length "L" of the monopole is inversely proportional to the driving frequency. Thus, for example, L is about 4 cm at 915 MHz. This value gives a real input impedance at the driving frequency (i.e., a resonance). It also provides a heating zone that is a few centimeters in length. The other end of the coaxial cable 70 is soldered to a standard coaxial connector 32' (type SMA) to provide connection to a larger feedline from the directional coupler 34. The coaxial cable assembly is placed inside a nylon catheter 74, which has been sealed at the distal end 76 to prevent direct contact with tissue.

FIG. 2 also shows the optional thermometry catheter 80 arranged adjacent to the applicator 22'. The catheter 80 includes a thermometry probe 82, known in the art, to measure the temperature of the heating zone created by the monopole 72.

Figure 2A:
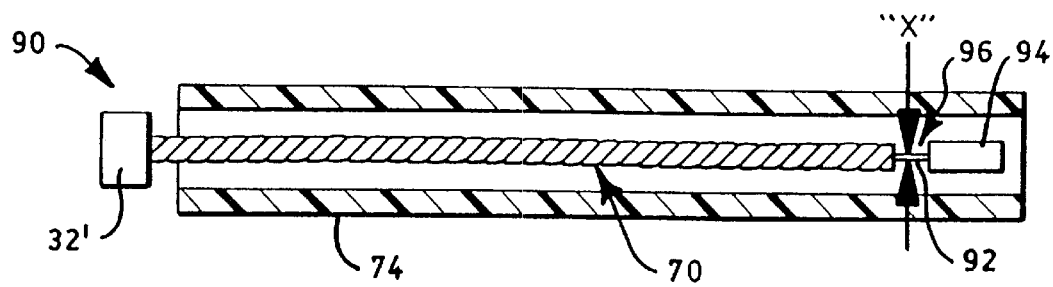
FIG. 2A shows an alternative applicator embodiment of the invention.

FIG. 2A shows another embodiment of an applicator 90 constructed according to the invention. The applicator 90 utilizes a monopole 92 of greater diameter "X"—as compared to the monopole 72 of FIG. 2—so that it has a shorter resonant length. The shorter length is convenient for placement in the organ to be heated. This applicator 90 is constructed as above, except that the insulation is removed from around the inner conductor 92 so that it can be soldered to a separate piece of outer shield material 94. A gap 96 is maintained between the monopole 92 and the shield 94 of the coaxial cable; and the assembly is configured within a sealed catheter 74.

Those skilled in the art should thus appreciate that the applicator 90, and certain other systems and applicators described herein, can be utilized in the treatment and heating of tissues other than the fallopian tube.

Figure 2B:
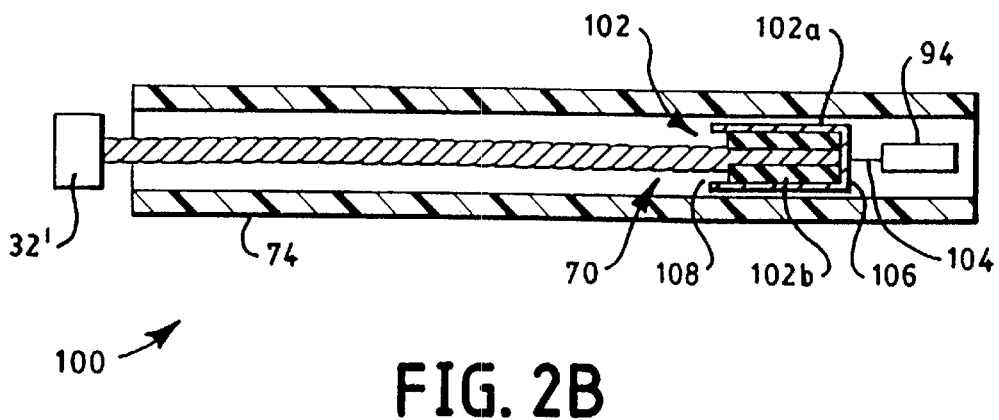
FIG. 2B shows another applicator embodiment of the invention.

A third applicator 100 is shown in FIG. 2B. The applicator 100 includes a choke 102 to reduce currents flowing from the distal monopole 104 back toward the insertion point into tissue. Such currents may heat overlying tissue that is not the target of the treatment. The choke 102 has a cylindrical conductor 102a surrounding the outer shield of the coaxial cable; but separated from it by an insulating layer 102b. The choke 102 is connected electrically to the outer shield at its distal end 106, but not at its proximal end 108.

Figure 2C:
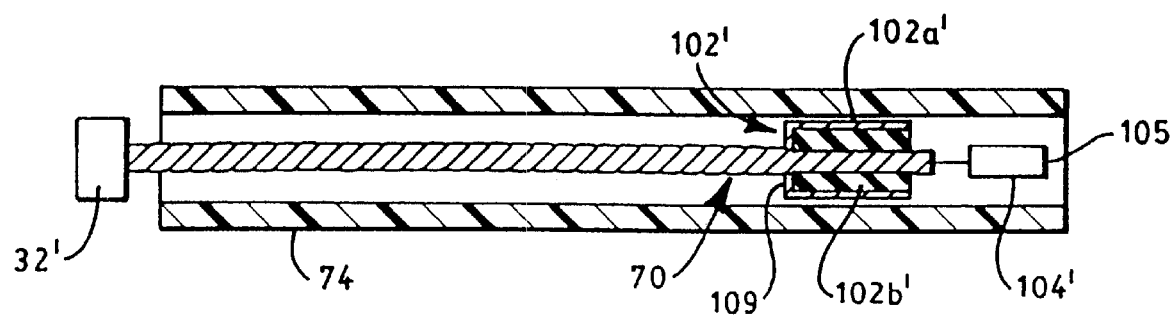
FIG. 2C shows an alternative choke arrangement, in accord with the invention.

FIG. 2C shows an alternative choke arrangement of the invention, where the choke 102' is inverted as compared to FIG. 2B. The applicator 100' of FIG. 2C operates similarly as in FIG. 2B, where currents from the distal end 105 of the monopole 104' are reduced towards the insertion point into tissue. The conductor 102a' connects to the center conductor at the proximal end 109 of the choke 102'.

Figure 2D:
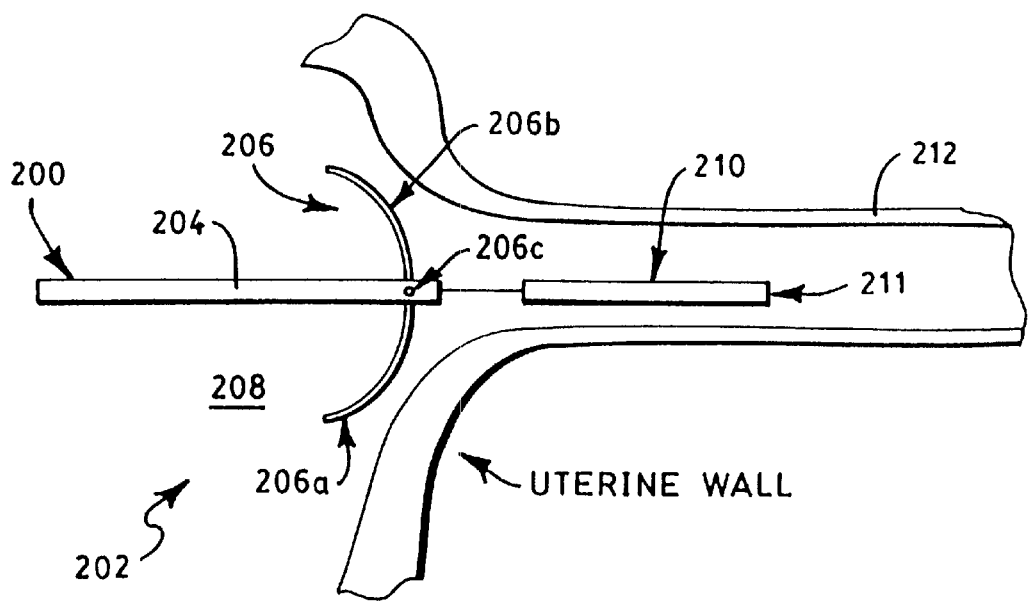
FIG. 2D illustrates a ground plane choke used with an applicator of the invention.

FIG. 2D shows an alternative configuration wherein a proximal end 200 of an applicator 202 (for example, utilizing a coaxial cable 204) includes a ground plane 206 (generally formed by wires 206a, 206b, 206c to form an approximate ground plane, wire 206c indicating out of page direction) deployed within the uterus 208 to reduce current flow back to the proximal end 200. The monopole antenna 210 functions as described above, with its distal end 211 within the fallopian tube 212. The wires 206a–c (shown illustratively with three wires, where fewer or greater numbers of wires can be used) are separated by less than a wavelength of the applied energy to approximate a solid ground plane.

Experimental Results

A microwave applicator was developed and tested in a rabbit model, with the goal of developing a system to sterilize a human female through a transvaginal-transcervical-transuterine retrograde technique. The clinical procedure would create an occluding lesion in the isthmic portion of the human fallopian tube in an out-patient procedure. The microwave applicator consisted of a flexible coaxial cable from which the inner conductor was extended to form a resonant monopole antenna. See, e.g., items 22' and 72 of FIG. 2. The coaxial cable and monopole were placed within a sealed teflon catheter of 3 mm diameter. See, e.g., item 74 of FIG. 2. A second parallel catheter of 1 mm diameter was secured to the first to provide guidance for a microwave-immune thermometry probe. See, e.g., item 80 of FIG. 2. Following laparotomy exposure, the applicator was placed with a transvaginal-transcervical retrograde technique in each uterine horn in succession. The temperature was elevated to 65 degrees C. for five minutes. Thirty days following treatment, there was marked constriction and discoloration of the treated site as well as significant architectural effacement of the tissue composing the uterine wall. In some cases, the uterine lumen was completely occluded.

By way of background, the microwave applicator of these tests heats tissue through a physical mechanism that does not depend on the flow of current from a metallic conductor in direct contact with tissue. In fact, the energy may pass through an insulating outer layer of the applicator, which is preferably biocompatible, for example, Teflon. The applicator system elevates the temperature of living tissue through absorption of microwave energy. The energy is delivered by the applicator when inserted into proximity with the tissue to be heated. The applicator of these experiments contains a coaxial cable for transferring microwave energy from a generator outside the body to the site of heating without significant deposition of energy in overlying tissue. At the site of intended heating, the applicator contains a monopole antenna for coupling microwave energy to the surrounding tissue without direct contact of a metal conductor with tissue.

The monopole is embedded in a cylinder of insulating, biocompatible material, such as polytetraflouroethylene (Teflon). At the site of intended heating, the oscillating current and charge on the monopole conductor produce oscillating electric and magnetic fields in the surrounding tissue. The oscillating electric field causes polar molecules in tissue, such as water, to rotate in place, generating frictional heating. The presence of an overlying layer of insulating material does not prevent the formation of electric and magnetic fields in tissue, because the length of the monopole is chosen to form a resonant or approximately resonant structure. Such a structure ensures coordination of the electric and magnetic fields such that they sustain themselves outside the applicator and thus radiate energy away from the applicator. The length of a resonant structure is inversely proportional to the microwave frequency and is inversely proportional to the square root of a weighted average of the permittivity (dielectric constant) of the insulating layer and the surrounding tissue. At 915 MHz or 2450 MHz (MHz=$10^6$ cycles/second), the length of an insulated monopole at or near resonance in tissue is one centimeter to several centimeters. These values of microwave frequency are those permitted by the FCC for use in industrial, scientific, or medical applications (ISM frequencies).

The microwave applicator used in these experiments is adequately shown in FIG. 2. It consisted of a 1.6 mm diameter, flexible, coaxial cable with an extension of the inner conductor to form a monopole at the location of intended energy deposition. The point at which the inner conductor emerges from the feedline is called the driving point, or junction. The coaxial cable was placed within one lumen of a "custom catheter"; a second lumen of the custon catheter was available for a thermometry probe with which to measure tissue temperature (note, those skilled in the art should appreciate that the two catheters 74, 80 of FIG. 2 can be combined into a single custom catheter with two lumens, one for the applicator 22' and one for the thermometry probe 82). The resonance length of the antenna can be computed as an inverse function of frequency. At the resonance length, the antenna deposits energy most efficiently. Preliminary calculations show this length to be approximately 3 cm at 915 MHz. In order to fit the anatomy of other subjects, it is desirable to use a shorter monopole, such as the next-highest ISM frequency of 2450 MHz.

The antenna was constructed from standard flexible coaxial cable (1.6 mm OD, 50 ohms), from which the outer braid was removed at the tip to form the monopole of resonance length. At the proximal end of the cable, we installed a standard, miniature microwave connector (SMA type) for connection to the microwave generator. The antenna was placed within a catheter of 2.2 mm outer diameter. We measured the impedance of the antenna over the frequency range 700 MHz to 1100 MHz with a Hewlett Packard Network Analyzer Model 8753C. The length of the distal section of the prototype antenna was trimmed or lengthened, as appropriate, to make the impedance purely real at 915 MHz. The voltage reflection coefficient was less than 0.1.

To characterize the heating pattern of the applicator, we immersed it in tissue-equivalent phantom, a semitransparent, viscous liquid mixture with the same conductivity and dielectric constant as soft tissue at microwave frequencies. The applicator was secured to a sheet of liquid crystal from Edmund Scientific, Barrington, N.J., which indicates temperature over a 5 degrees C. range with a calibrated color change. The liquid crystal sheet had a rectangular cut-out to accommodate the applicator in a plane parallel to its long axis. We photographed the liquid crystal sheet at 2 minutes after application of 30 watts of microwave power in order to visualize the heating pattern of the applicator. We found the length heated above 40 degrees C. at 2 minutes was a 3 cm zone extending 2 cm proximal to the junction.

After the first heating of a rabbit, we constructed a second applicator in the form of a choked dipole in order to prevent significant energy deposition on the feedline. The choke consisted of a new cylindrical conductor insulated from the feedline by a dielectric layer (see, e.g., FIG. 2A). The new conductor was electrically connected to the feedline only at the antenna junction. The gap between the feedline and new conductor had a length of approximately one quarterwavelength; consequently, an approximate choke, or open circuit, is formed on the feedline, according to transmission line theory. This approximate choke tends to block the microwave current that otherwise would flow on the feedline and heat tissue proximal to the target zone. We refer to this applicator below as the choked dipole. This antenna was inserted in a catheter of 3 mm OD. As noted above, the length of this heating zone may be greater than required ultimately in a clinical system and is a practical consequence of our use of 915 MHz in these experiments. The microwave applicator we designed allowed us to perform experiments of microwave heating in vivo.

Other components used in the experiments of this section are shown in FIG. 1.

We chose anestrus rabbits as the animal model for the following reasons: the uterine horn of the anestrus rabbit is similar in size and shape to the isthmic segment of the human fallopian tube; the animal can be maintained easily in anestrus; experimental manipulation is technically easy and morbidity tends to be extremely low; and the animals are colony bred, thus allowing selection for age and weight uniformity. Pre-estrous female rabbits (3.5 to 5 kg) were purchased from Milbrook Farms (Amherst, Mass.). All treatments were performed under general anesthesia, which consisted of ketamine/xylazine (2.0/0.2 mg/kg IM) induction followed by intubation and maintenance anesthesia (1.5% halothane/100% oxygen). All rabbits were prepared for laparotomy using standard aseptic techniques. A midline incision was made, then the bladder was elevated out of the incision and separated from the lower uterine segment. The uterus was isolated, and connective tissue was dissected away to allow a nearly straight insertion into one uterine horn with a transvaginal-transcervical approach. The microwave catheter was then inserted. The uterine horn was isolated thermally from adjacent bowel and bladder by saline-filled balloons packed around the horn. After the microwave heat treatment, an ovarectomy was performed.

All animals survived the experimental treatments without serious morbidity, and were sacrificed with intravenous KCl, following deep anesthesia, at 31 (+/−4) days after treatment. Immediately following euthanasia, each uterus was removed en bloc. The tissue was placed in neutral 4% neutral buffered formaldehyde and submitted for histologic processing. Five tissue sections were taken from the lesioned or control segment in each horn. Representative histologic sections were taken through the treated region, as well as proximal and distal to the treated area.

Treatment Protocol

Rabbit I was treated with the unchoked monopole of FIG. 2A in both uterine horns. In the left horn, a maximum temperature of 65 degrees C. was maintained for 10 minutes by applying 7 watts of forward microwave power at 915 MHz. In the right horn, a maximum temperature of 70 degrees C. was maintained for 5 minutes by applying 10 watts of forward microwave power. The reflected power was approximately 10%.

Rabbits II through IV were treated with the choked dipole of FIG. 2B in both uterine horns. The target temperature, time at target temperature, and microwave power for each horn in each subject are shown in Table 1. Reflected power was approximately 10%. In five of the six treatments in Rabbits II through IV, the temperature distribution adjacent and parallel to the microwave catheter was measured in the steady-state.

TABLE 1

Summary of Rabbit Treatments

| Rabbit | Applicator | Horn | Target | Time | Power |
|--------|------------|------|--------|------|-------|
| I | Unchoked | left | 65 deg. C. | 10 min | 7 W |
| | | right | 70 deg. C. | 5 min | 10 W |
| II | Choked | left | 65 deg. C. | 5 min | 33 W |
| | | right | 75 deg. C. | 8 min | 50 W |
| III | Choked | left | 65 deg. C. | 6 min | 40 W |
| | | right | 55 deg. C. | 5 min | 20 W |
| IV | Choked | left | 70 deg. C. | 5 min | 30 W |
| | | right | 70 deg. C. | 5 min | 30 W |

Results

The longitudinal temperature distribution measured in the steady-state at the surface of the microwave catheter had a maximum value located approximately at the antenna junction; temperature values decreased distal and proximal to the junction. To quantify the length of the temperature distribution, the value of body temperature was subtracted from the maximum temperature, and this value was divided by two to yield a quantity defined as DT50. The length along the applicator surface at which temperatures above DT50 were measured was defined as L50. For five treatments with the choked dipole, the average value of L50 was 5.3 cm +/−0.8 cm. Lesions were observed on the serosa of the uterine horn immediately after treatment. The average length of lesion was 3.8 cm +/−1.5 cm, and the location of the lesion center was on average 1.6 cm +/−0.5 cm proximal to the applicator junction. The lesions did not extend around the entire circumference of the horn, but instead involved a quarter or half arc of a circle. No charring of tissue was observed at any location in any of the treatments.

After sacrifice, gross assessment of the treated uteruses showed pale discoloration and a markedly reduced circumference of the treated segment of uterus horn. The normal uterine anatomy contains numerous folds and villi covered by specialized columnar epithelium on the surface and numerous glands in the submucosa. By contrast, the 30-day post-treatment uterine horns showed very marked edema and vascular dilitation resulting in significant thickening of the submucosa, near complete loss of the submucosal glands and the covering epithelium and the influx of a mixed inflammatory infiltrate. These pathologic changes generally resulted in extensive architectural effacement of the inner portion of the uterine wall anatomy and occlusion of all or part of the lumen space. In some cases, the tissue damage and resultant healing were significant enough to cause complete occlusion of the lumen. In these instances, the lumen and adjacent tissues were completely replaced by fibrosis and inflammation.

Discussion

In the first rabbit, acute blanching of the overlying bowel was observed, indicating significant thermal damage beyond the target tissue. In subsequent experiments, the uterine horn was isolated thermally to allow study of only the target tissue. Other experimentation will reduce the thermal dose, while still producing blockage of the horn, or will devise a modified technique to avoid thermal damage to overlying bowel. In contrast to the effects of RF heating, no charring of tissue was observed. The length of the heated zone we observed was suitable for a study of tissue effects, but it may be too long for tubal occlusion in a human patient. In future studies, we plan to use a generator operating at 2450 MHz, since the resonance dipole length and hence value of L50 will decrease in inverse proportion. External lesion formation appears to be sensitive to the degree of contact of the applicator within the horn, since lesions did not form around the entire circumference. However, this did not seem to affect effacement or internal occlusion of the horn. We believe that highly-controlled microwave hypethermia may be used to safely and effectively occlude the human fallopian tube in an out-patient setting. While indicating the need for further refinement and testing, the results presented here suggest not only that the anestrous rabbit uterus is an appropriate and useful animal model for studying human fallopian tube occlusion, but that complete tubal occulsion can be produced accurately and effectively with the appropriate microwave applicator. Our initial experimental treatments were not without complications, including acute blanching of the bowel overlying the treated portion of uterus. This effect demonstrated the potential for significant thermal damage beyond the target if an inappropriate thermal dose was used. In subsequent experiments, the uterine horn was isolated from the bowel to allow for a more intense study of the microwave hyperthermia effects in the target tissue (uterus), without the risk of damaging a critical organ.

Conclusions

In these experiments, a microwave applicator within a 3 mm OD catheter has been developed for inducing thermal blockage of the uterine horn of a rabbit. When a maximum temperature of 70 deg.C was maintained for 5 minutes, the architecture of the uterine horn was completely effaced four weeks after treatment. During the treatment, no charring of tissue occurred and no associated self-limiting of heating occurred, as has been observed with radio-frequency applicators. Overlying bowel was damaged during one treatment, in which the uterine horn was not thermally isolated.

Additional background for the invention may be found with reference to the following article, incorporated herein by reference and written by the inventors hereof: Manganiello et al., A Bipolar Radiofrequency Catheter Fails to Occlude a Feline Uterine Horn: A Model for Fallopian Tube Occlusion, Journal of the American Association of Gynecologic Laparoscopists, Vol. 5, No. 3, 25–28 (August 1998).

The invention thus provides several advantages, including: 1) the methods herein can be performed in an outpatient setting with little or no morbidity, 2) the methods herein eliminate the need for a general anesthetic 3) the invention is cost effective, 4) the invention is simple and easy to perform. and 5) the invention assures reliable contraception.

The invention thus attains the objects set forth above, among those apparent from the preceding description. Since certain changes may be made in the above methods and systems without departing from the scope of the invention, it is intended that all matter contained in the above description or shown in the accompanying drawing be interpreted as illustrative and not in a limiting sense. It is also to be understood that the following claims are to cover all generic and specific features of the invention described herein, and all statements of the scope of the invention which, as a matter of language, might be said to fall there between.

Having described the invention, what is claimed is:

1. A method for non-invasive occlusion of a fallopian tube, comprising the steps of:
   inserting an assembly of electrical conductors into the fallopian tube, the conductors forming a microwave antenna; and
   driving the conductors with microwave frequencies wherein the antenna emits microwave radiation that heats the fallopian tube for delayed occlusion of the fallopian tube.

2. A method according to claim 1, comprising the further step of shielding the conductors within a distal end of a biocompatible catheter to prevent direct contact between the conductors and tissue.

3. A method according to claim 2, further comprising the step of visualizing placement of the distal end within the fallopian tube through an imaging catheter during the step of inserting.

4. A method according to claim 2, farther comprising the step of fluoroscopically estimating placement of the distal end within the fallopian tube during the step of inserting.

5. A method according to claim 1, wherein the step of driving comprises driving the conductors at an ISM frequency.

6. A method according to claim 5, wherein the step of driving comprises driving the conductors at 915 MHz.

7. A method according to claim 5, comprising the step of driving the conductors at 2450 MHz.

8. A method according to claim 1, wherein the step of driving extends for approximately five minutes.

9. A method according to claim 1, wherein the delayed occlusion occurs between approximately 30 and 60 days.

10. A method according to claim 1, wherein the step of inserting the conductors comprises inserting a distal end of a coaxial cable, a center conductor of the coaxial cable forming a monopole conductor, the center conductor extending from the distal end of the coaxial cable for a length corresponding to a desired resonant frequency.

11. A method according to claim 1, wherein the step of inserting the conductors comprises inserting a catheter into the fallopian tube via transvaginal-transcervical-transuterine technique.

12. A method of claim 1, further comprising the step of depositing one to ten watts of microwave power in the fallopian tube.

13. A method according to claim 1, further comprising the step of heating tissue within the fallopian tube to between approximately 60 and 80 degrees C. for approximately two to ten minutes.

14. A method according to claim 1, farther comprising the step of measuring tissue temperature during the step of driving the conductors.

15. A method according to claim 14, further comprising the step of utilizing a microwave-immune thermometry system to measure the temperature.

16. A method according to claim 1, further comprising utilizing a monopole antenna as the assembly of electrical conductors.

17. A method according to claim 1, further comprising driving the conductors with approximately 35 watts of power such that between approximately two and ten watts of power deposits within the fallopian tube.

18. A method according to claim 1, wherein the step of inserting comprises inserting the conductors into the isthmic portion of the fallopian tube.

19. A system for occluding the fallopian tube, comprising:
an applicator having a distal end for placement into the fallopian tube, and a proximal end for manipulating the applicator,
an assembly of conductors, disposed within the distal end of the applicator, for depositing microwave energy into the tissue of the fallopian tube without physical contact between the conductors and the tissue, the microwave energy heating the tissue for subsequent tubal occlusion.

20. The system of claim 19, wherein the applicator comprises an elongated catheter.

21. The system of claim 20, wherein the catheter has a diameter in a range of about from 1 mm to 3 mm.

22. The system of claim 20, wherein the catheter is disposable after one treatment.

23. The system of claim 19, further comprising a microwave generator for driving the conductors at the drive frequency.

24. The system of claim 19, wherein the conductors comprise one end of a center conductor of a coaxial cable.

25. The system of claim 20, wherein the catheter comprises biocompatible material.

26. The system of claim 25, wherein the material comprises Teflon.

27. The system of claim 19, further comprising a power control section for driving the conductors at the drive frequency.

28. The system of claim 27, wherein the power control section further comprises means for controlling power delivered to the tissue to ensure proper temperature treatment of the tissue.

29. The system of claim 28, wherein the power control section further comprises a controller, the controller having a dual directional coupler, a forward power meter, and a reflected power meter, the coupler diverting a fraction of microwave power to both power meters to assess normal function of the conductors, as determined by a ratio of reflected power to forward power less than about 0.1.

30. The system of claim 19, further comprising a microwave immune-thermometry probe constructed and arranged within the applicator, for measuring temperature of the tissue.

31. The system of claim 19, farther comprising a fiber optic probe constructed and arranged adjacent to the conductors for measuring temperature of the tissue.

32. The system of claim 19, further comprising (i) a flexible coaxial cable, the conductors being formed from an extension of a conductor of the cable at a distal end of the cable, and (ii) a coaxial connector, for connecting the cable to a microwave generator.

33. The system of claim 20, wherein the catheter comprises means for sealing the catheter at its distal end to prevent contact between the conductors and the tissue.

34. The system of claim 19, wherein the conductors have a diameter X and a length L, the parameters X and L being selected to provide resonance at the drive frequency and being sized to correspond to a length of the isthmic region of the fallopian tube.

35. The system of claim 19, further comprising a flexible coaxial cable having an outer insulator and an inner conductor, the conductors being formed from an extension of the inner conductor, further comprising an outer shield attached to the antenna such that a gap is formed between the shield and the insulator.

36. The system of claim 20, further comprising a choke attached proximal to the conductors to reduce currents flowing from the distal end back towards the proximal end of the catheter.

37. The system of claim 36, wherein the choke comprises (i) a cylindrical conductor surrounding an outer shield of the coaxial cable and separated from the shield via an insulating layer, the cylindrical conductor having a distal end positioned towards the distal end of the catheter and a proximal end positioned towards the proximal end of the catheter, and (ii) means connecting the cylindrical conductor to the shield at the distal end of the choke.

38. The system of claim 36, wherein the choke comprises (i) a cylindrical conductor surrounding an outer shield of the coaxial cable and separated from the shield via an insulating layer, the cylindrical conductor having a distal end positioned towards the distal end of the catheter and a proximal end positioned towards the proximal end of the catheter, and (ii) means connecting the cylindrical conductor to the shield at the proximal end of the choke.

39. The system of claim 19, wherein the conductors comprise one end of a center conductor of a coaxial cable, and further comprising a ground plane attached to the outer conductor of the cable and deployed in the uterus connected with the fallopian tube to reduce currents flowing from the distal end back toward the proximal end of the catheter.

40. The system of claim 39, wherein the ground plane comprises wires separated by less than a wavelength of the energy so as to approximate a solid ground plane effect.

* * * * *

UNITED STATES PATENT AND TRADEMARK OFFICE
CERTIFICATE OF CORRECTION

PATENT NO.   : 6,485,486 B1
DATED        : November 26, 2002
INVENTOR(S)  : B. Stuart Trembly, Paul Manganlello and P. Jack Hoopes It is certified that error appears in the above-identified patent and that said Letters Patent is hereby corrected as shown below:

<u>Column 14,</u>
Line 1, "farther," should read -- further --

Signed and Sealed this

Twenty-eighth Day of June, 2005

JON W. DUDAS
*Director of the United States Patent and Trademark Office*